United States Patent
Hanson et al.

(10) Patent No.: US 6,310,271 B1
(45) Date of Patent: Oct. 30, 2001

(54) POLYNUCLEOTIDES ENCODING CHOLINE MONOOXYGENASE AND PLANTS TRANSFORMED THEREWITH

(75) Inventors: Andrew D. Hanson; Bala Rathinasabapathi, both of Gainesville, FL (US); Michael Burnet, Les Hameaux (FR)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 09/004,393

(22) Filed: Jan. 8, 1998

Related U.S. Application Data

(60) Provisional application No. 60/035,147, filed on Jan. 8, 1997.

(51) Int. Cl.[7] .............................. C12N 15/29; C12N 5/04; C12N 15/82; A01H 5/00; A01H 5/10

(52) U.S. Cl. ................... 800/278; 435/69.1; 435/468; 435/410; 435/419; 536/23.1; 536/23.6; 800/285; 800/290; 800/295; 800/306; 800/312; 800/314; 800/317.2; 800/317.3; 800/317.4; 800/320; 800/320.1; 800/320.2; 800/320.3; 800/322

(58) Field of Search .............................. 536/23.6, 23.1; 800/279, 278, 285, 290, 295, 306, 312, 314, 317.2, 317.3, 317.4, 320, 320.1, 320.2, 320.3, 322

(56) References Cited

PUBLICATIONS

Corcuera, L.J. (1993) "Biochemical Basis for the Resistance of Barley to Aphids" Phytochem 33:741–747.

Hanson, A.D., Hitz, W.D. (1982) "Metabolic Responses of Mesophytes to Plant Water Deficits" Annu. Rev. Plant Physiol. 33:163–203.

Hayashi, H. et al. (1997) "Transformation of *Arabidopsis thaliana* with the codA gene for choline oxidase; accumulation of glycinebetaine and enhanced tolerance to salt and cold stress" The Plant Journal 12:133–142.

Kishor, P.B.K. et al. (1995) "Overexpression of $\Delta^1$–Pyrroline–5–Carboxylate Synthetase Increases Proline Production and Confers Osmotolerance in Transgenic Plants[1]" Plant Physiol. 108:1387–1394.

Lilius, G. et al. (1996) "Enhanced NaCl Stress Tolerance in Transgenic Tobacco Expressing Bacterial Choline Dehydrogenase" Bio/Technology 14:177–180.

Mackay, M.A. et al. (1984) "Organic Osmoregulatory Solutes in Cyanobacteria" Journal General Microbiology 130:2177–2191.

Pearce, R.B. et al. (1976) "Glycinebetaine and Choline in Wheat: Distribution and Relation to Infection by Fusarium Graminearum" Phytochemistry 15:953–954.

Rozwadowski, K.L. et al. (1991) "Choline Oxidase, a Catabolic Enzyme in *Arthrobacter pascens*, Facilitates Adaptation to Osmotic Stress in *Escherichia coli*" Journal of Bacteriology 173:472–478.

Tarczynski, M.C. et al. (1993) "Stress Protection of Transgenic Tobacco by Production of the Osmolyte Mannitol" Science 259:508–510.

Warr, S.R. C. et al. (1988) "The compatibility of osmotica in cyanobacteria" Plant Cell and Environment 11:137–142.

Rathinasabapathi, B. et al. (1997) "Choline monooxygenase, an unusual iron–sulfur enzyme catalyzing the first step of glycine betaine synthesis in plants: Prosthetic group characterization and cDNA cloning" Proc. Natl. Acad. Sci. USA 97(7):3454–3458.

Russell, B.L. et al. (1997) "Osmotic stress induces expression of choline monooxygenase in sugar beet and amaranth" EMBL Database; EMPLN: AF023132; Accession No.: AF023132.

Wilson, R. et al. (1995) "2.2 Mb of contiguous nucleotide sequence from chromosome III of C. elegans" EMBL Database; EMINV: CEC18D1; Accession No.: Z48543.

Wilson, R. et al. (1996) "2.2 Mb of contiguous nucleotide sequence from chromosome III of C. elegans" EMBL Database; EMINV: CEF40D4; Accession No.: Z81536.

Rathinasabapathi, B. et al. (1993) "Cultivated and wild rices do not accumulate glycinebetaine due to deficiencies in two biosynthetic steps" Crop Science 33:534–538.

Burnet, M. et al. (1995) "Assay, purification and partial characterization of choline monooxygenase from spinach" Plant Physiology 108:581–588.

Weretilnyk, E.A. and Summers, P.S. (1992) "Betaine and choline metabolism in higher plants" Current Topics in Plant Physiology 7:89–97.

*Primary Examiner*—Paula K. Hutzell
*Assistant Examiner*—Ousama Zaghmout
(74) *Attorney, Agent, or Firm*—Saliwanchik, Lloyd & Saliwanchik

(57) ABSTRACT

A full length choline monooxygenase (CMO) cDNA was cloned from spinach and used to transform plants which do not naturally express CMO. A method is presented to improve stress tolerance of crops following engineering of CMO and BADH in plants that lack glycine betaine accumulation. Also provided are fragments useful as probes to isolate other CMO-type genes, and antisense sequences which inhibit the production of CMO. Reduction of glycine betaine as a consequence of antisense expression of CMO in species naturally accumulating glycine betaine, improves the transgenic plant's tolerance toward pathogens and pests and/or enhances its nutritional quality.

48 Claims, 5 Drawing Sheets

```
TAGTAAGGGTGTAGCTAATTAGCAAAATAAACAAAAAGGAAGTGTTGAGTTGGTTAATGA        60
                                                        M  M         2
TGGCAGCAAGCGCAAGCGCAACCACAATGTTGCTAAAATACCCAACTACAGTTTGTGGTA       120
 A  A  S  A  S  A  T  T  M  L  L  K  Y  P  T  T  V  C  G  I        22
TTCCAAATCCTTCATCAAACAATAATAATGATCCTTCAAACAATATAGTTTCTATTCCAC       180
 P  N  P  S  S  N  N  N  D  P  S  N  N  I  V  S  I  P  Q           42
AAAATACTACTAATCCAACACTTAAGTCCCGTACACCTAATAAAATCACCACCAACGCCG       240
 N  T  T  N  P  T  L  K  S  R  T  P  N  K  I  T  T  N  A* V        62
TCGCGGCACCGTCCTTTCCTTCTTTAACCACCACTACACCGTCGTCCATCCAATCACTTG       300
 A  A  P  S  F  P  S  L  T  T  T  T  P  S  S  I  Q  S  L  V        82
TCCACGAATTCGACCCTCAAATTCCCCCTGAAGACGCTCATACACCTCCTAGCTCTTGGT       360
 H  E  F  D  P  Q  I  P  P  E  D  A  H  T  P  P  S  S  W  Y       102
ATACCGAACCTGCCTTCTATTCCCATGAACTTGAGCGTATCTTTTATAAAGGATGGCAAG       420
 T  E  P  A  F  Y  S  H  E  L  E  R  I  F  Y  K  G  W  Q  V       122
TTGCAGGGATCAGCGATCAAATAAAAGAGCCTAACCAATATTTCACTGGCAGCTTAGGAA       480
 A  G  I  S  D  Q  I  K  E  P  N  Q  Y  F  T  G  S  L  G  N       142
ATGTTGAATATTTGGTGTCTCGAGATGGTGAAGGGAAAGTTCATGCATTTCACAATGTTT       540
 V  E  Y  L  V  S  R  D  G  E  G  K  V  H  A  F  H  N  V  C†      162
GCACCCATCGTGCATCTATTCTTGCTTGCGGTAGTGGCAAAAAGTCGTGTTTCGTGTGCC       600
 T  H† R  A  S  I  L  A  C  G  S  G  K  K  S  C  F  V  C† P       182
CTTACCATGGATGGGTATATGGCATGGACGGATCACTTGCGAAAGCCTCCAAAGCAAAAC       660
 Y  H† G  W  V  Y  G  M  D  G  S  L  A  K  A  S  K  A  K  P       202
CTGAACAAAACTTGGATCCTAAAGAACTTGGGCTTGTACCCCTAAAAGTTGCAGTATGGG       720
 E  Q  N  L  D  P  K  E  L  G  L  V  P  L  K  V  A  V  W  G       222
GGCCGTTCGTTCTTATCAGCTTGGACAGATCACTTGAAGAAGGTGGTGATGTTGGAACTG       780
 P  F  V  L  I  S  L  D  R  S  L  E  E  G  G  D  V  G  T  E       242
AGTGGCTTGGTACTTCTGCTGAAGATGTTAAGGCCCATGCTTTTGATCCTTCACTTCAAT       840
 W  L  G  T  S  A  E  D  V  K  A  H  A  F  D  P  S  L  Q  F       262
TCATTCACAGAAGTGAATTCCCAATGGAATCTAATTGGAAGATTTTCAGTGACAACTACT       900
 I  H  R  S  E  F  P  M  E  S  N  W  K  I  F  S  D  N  Y  L       282
TGGATAGCTCATATCATGTTCCTTATGCACACAAATACTATGCAACTGAACTCAACTTTG       960
 D  S  S  Y  H  V  P  Y  A  H  K  Y  Y  A  T  E  L  N  F  D       302
ACACTTACGATACCCAAATGATCGAAAACGTTACAATTCAAAGAGTGGAAGGAAGTTCAA      1020
 T  Y  D  T  Q  M  I  E  N  V  T  I  Q  R  V  E  G  S  S  N       322
ACAAGCCTGATGGTTTTGATAGAGTTGGAATTCAAGCATTCTATGCTTTCGCGTATCCAA      1080
 K  P  D  G  F  D  R  V  G  I  Q  A  F  Y  A  F  A  Y  P  N       342
ATTTCGCTGTGGAAAGGTATGGCCCTTGGATGACTACAATGCATATTCACCCATTAGGAC      1140
 F  A  V  E  R  Y  G  P  W  M  T  T  M  H  I  H  P  L  G  P       362
CAAGGAAATGCAAACTAGTGGTGGACTATTATATTGAAAATTCTATGTTGGATGACAAGG      1200
 R  K  C  K  L  V  V  D  Y  Y  I  E  N  S  M  L  D  D  K  D       382
ATTACATCGAGAAGGGCATAGCAATCAATGATAACGTACAGAGGGAAGATGTGGTGCTGT      1260
 Y  I  E  K  G  I  A  I  N  D  N  V  Q  R  E  D  V  V  L  C       402
GTGAAAGTGTACAAAGAGGTTTGGAGACACCAGCATATCGTAGTGGGAGATATGTGATGC      1320
 E  S  V  Q  R  G  L  E  T  P  A  Y  R  S  G  R  Y  V  M  P       422
CTATTGAGAAAGGAATCCACCATTTCCACTGCTGGTTGCAACAAACTTTGAAGTAA TGT      1380
 I  E  K  G  I  H  H  F  H  C  W  L  Q  Q  T  L  K                439
TGACTTGACTTCACCGGACGTTTGCGTGCTCCTCTTGGCTCTTGCAGTTAGTTATGTGTG      1440
TATGCTCATGGCCTAAACTTATAACATTTTATACTCAATTTATAATAAACACCATAGTAA      1500
GTACCTCAGATATCCCGTGCATTTTCATTTTCAGGGGAAATAA TGACATTGTCTATCAA      1559
TATCAATATCAATATCAATATTACCAGTAATTTTAAACAAAAAAAAAAAAAAAA            1619
AAA                                                                1622
```

FIG. 2

```
   1  ctcgtgccga attcggcacg agaaaatcta gtaacaatgg cagcaagtgc tacaaccatg
  61  ttgctcaaat acccaactct ttgtgctatg ccaaattcct cttcatcttc aaacaacaac
 121  gatcttccta ctagcattcc tcttaataac aataacaatt tattatcaaa caaaaacaaa
 181  attcttcaaa caccaaatat taatacttct actaataaaa tcatcactaa agctgttgct
 241  tccsctgttt ttccaactct aaaaaccaca tccaacacac cttcttccat tcgatcactt
 301  gttcatgaat tcgaccccga aattccacct gaagatgctc ttacacctcc tagtacttgg
 361  tacactgagc ctgccttta ttcccatgaa cttgaacgta tcttttacaa aggatggcaa
 421  gttgcaggct actctgagca agtaaaggag aaaaatcaat atttcactgg cagtttaggg
 481  aatgttgaat atttagtatc tcgagatggt caaggcgaac ttcatgcatt tcacaatgtt
 541  tgtacacatc gtgcatcaat tcttgcttgt ggaagtggca aaaagtcatg tttcgtatgc
 601  ccttaccatg gatgggtgta tggcttagat ggatcactcg ccaaagccag caaagcaact
 661  gaaacacaaa atttggatcc taaagaactt gggcttgcac ccctaaaagt tgcagaatgg
 721  ggcccattca ttcttatcag cttggaccga tctctagatg ctaatgctga tgttggaaca
 781  gagtggattg gtaaatctgc agaagatgtt aaggcccatg cttttgatcc taatctaaag
 841  ttcacccata gaagtgaatt cccaatggaa tgcaactgga aggttttctg tgataactat
 901  ctggatagct cttaccatgt tccttatgct cacaaatact atgcagctga actcgacttt
 961  gacacttaca acactgaaat gatcgagaaa tgtgtgattc aaagagttgg tagcagttca
1021  aacaagccag atggatttga tagacttgga actgaagcat tctatgcttt tatttacccc
1081  aactttgctg tggaaaggta tggcacttgg atgactacaa tgcatgtcgt tcctatggga
1141  caaaggaaat gcaaactagt ggtggactat tatcttgaga aagccatgtt ggacgacaag
1201  gcttacattg acaagggcat agcaatcaac gataacgtgc agaaggaaga taaggtgttg
1261  tgtgaaagtg tccaaggggg actggagaca ccagcatacc gcagtggcag atatgtgatg
1321  ccaattgaga aaggaatcca ccacttccac tgttggttgc atgaaacttt gcagtgattt
1381  tcgggagctt atttctatgg ttttaccatg tcacattaat aatataattg atgttgggtt
1441  gagcctatgc tcctcatgca attaagttat tttgtggtca tgggaaaacc cttccatttc
1501  tagtatagta gtagtgtctg gtgctaatgt cccatataaa taaaagccat agcacctagt
1561  ttccccttca aagttatatc ctaaatattt atggggaaca tatgagattg agtatgaaca
1621  ttttatctag gcatatgtgt gatttttaat ttctttgaac aatgagggta agatttttgt
1681  ggatgttcgt cagattttat tttactattt atagtagaaa ttgctccaat tataaaaaaa
1741  aaaaaaaaaa a//
```

FIG. 4

MAASATTMLLKYPTLCAMPNSSSSSNNNDLPTSIPLNNNNNLLSNKNKILQTPNI
NTSTNKIITKAVASPVFPTLKTTSNTPSSIRSLVHEFDPEIPPEDALTPPSTWYTEPA
FYSHELERIFYKGWQVAGYSEQVKEKNQYFTGSLGNVEYLVSRDGQGELHAFH
NVCTHRASILACGSGKKSCFVCPYHGWVYGLDGSLAKASKATETQNLDPKELGL
APLKVAEWGPFILISLDRSLDANADVGTEWIGKSAEDVKAHAFDPNLKFTHRSEF
PMECNWKVFCDNYLDSSYHVPYAHKYYAAELDFDTYNTEMIEKCVIQRVGSSS
NKPDGFDRLGTEAFYAFIYPNFAVERYGTWMTTMHVVPMGQRKCKLVVDYYL
EKAMLDDKAYIDKGIAINDNVQKEDKVLCESVQRGLETPAYRSGRYVMPIEKGI
HHFHCWLHETLQ

FIG. 5

POLYNUCLEOTIDES ENCODING CHOLINE MONOOXYGENASE AND PLANTS TRANSFORMED THEREWITH

This application claims the benefit of U.S. Provisional Application No. 60/035,147 filed Jan. 8, 1997.

The subject invention was made with government support under a research project supported by the U.S. Department of Agriculture National Research Initiative Competitive Grants Program Grant No. 95-37100-1596. Mass spectral data were acquired at the Michigan State University-National Institutes of Health (NIH) Mass Spectrometry Facility, which is supported by NIH grant RR 00484. The government has certain rights in this invention.

FIELD OF THE INVENTION

BACKGROUND OF THE INVENTION

While the world population is constantly increasing, the need for food to feed this growing population directly increases as well. One unfortunate side effect correlated with increased populations is the rapid dwindling of available crop producing farm land. For instance, land in certain countries of Africa and Asia once marginally able to support food crops only decades ago is now completely arid and infertile, making crop production impossible. Unless drastic measures are taken, this situation is only going to worsen with growing populations.

In an effort to better current conditions and to stave off any exacerbation of the problem, much interest has been directed toward ways in which to optimize food production in harsh, barren conditions. The principle is that land currently unable to support crops might be utilized for cultivation. Current research involves looking at the defense mechanisms plants naturally use to survive in stressful environmental conditions and to determine whether these natural mechanisms can be exploited artificially, e.g., by cross-breeding or gene transformation, thereby producing more robust crops. One such defense mechanism which displays promise is organic solute accumulation.

When bacteria, marine algae, and many higher plants are exposed to salinity or drought, they accumulate organic solutes. These solutes include polyols, proline, and quaternary ammonium compounds. They are thought to confer stress tolerance to the organism by balancing the osmotic pressures between the outside and the inside of their cells, thus enabling them to maintain turgor and growth. Unsurprisingly, the biosynthetic pathways for these osmoprotective compounds have become targets for metabolic engineering to improve the stress tolerance of a target species. To date, there have been preliminary studies that have shown these pathways can be genetically manipulated in higher plants and that this can improve tolerance to various abiotic stresses (Tarczynski et al., 1993; Kishor et al., 1995; Lilius et al., 1996; Hayashi et al., 1997).

There is evidence to suggest that the quaternary ammonium compound glycine betaine may be a more effective osmoprotectant than polyols or proline (Mackay et al., 1984; Warr et al., 1988). Further, glycine betaine is more attractive as a potential genetic engineering target because, unlike proline or polyols, glycine betaine has no subsequent metabolic fate. Thus, in principle, this makes it simpler to engineer glycine betaine accumulation because its rate of degradation is not a concern.

In plants, as in bacteria, glycine betaine is synthesized by a two-step oxidation of choline. The first step (oxidation of choline to betaine aldehyde) is catalyzed by choline monooxygenase (CMO). The second step (oxidation of betaine aldehyde to glycine betaine) is catalyzed by betaine aldehyde dehydrogenase (BADH).

Certain higher plants, e.g., spinach and sugar beet, accumulate glycine betaine in response to osmotic stress. But many other species including tomato, tobacco, potato, legumes, rice, and some cultivars of corn and sorghum lack an ability to synthesize it. Metabolic engineering of glycine betaine synthesis in these crops could therefore improve their stress tolerance. Although bacterial choline oxidases (Rozwadowski et al., 1991; Hayashi et al., 1997) or dehydrogenases (Lilius et al., 1996) are being explored for this purpose, use of CMO (in conjunction with BADH) is preferable for the following reason. CMO requires for its function reduced ferredoxin from the light reactions of photosynthesis. Thus, CMO links glycine betaine synthesis with the light reactions of photosynthesis. This helps to match the supply of glycine betaine with the demand for osmotic adjustment and osmoprotection, which climbs rapidly after sunrise as the water potential and water content of salt- or drought-stressed leaves start falling (Hanson and Hitz, 1982).

In some circumstances, however, the synthesis of glycine betaine is an unwanted occurrence. For instance, in sugar manufacturing from beet, glycine betaine is one component of sugarbeets which complicates processing of sugar by inhibiting the crystallization of sugar. Hence sugar beet cultivars with no or reduced levels of glycine betaine in the roots will be desirable.

It has been suggested that glycine betaine accumulation may make plants susceptible to insect pests (Corcuera, 1993) or microbial pathogens (Pearce et al., 1976). Hence, under certain circumstances, it may be possible to improve a plant's resistance to pests or pathogens by blocking the synthesis of glycine betaine. The potential for such an application is available for many important crops that naturally accumulate glycine betaine, for example, wheat, barley, corn, sugarcane, sugar beet, spinach, cotton and sunflower.

Blocking CMO in crop species used as animal feed may also improve their nutritional value. Choline is a frequent animal feed supplement, and therefore cells which contain a higher concentration of choline by virtue of blocking its conversion into glycine betaine would be desirable. Accordingly, a process of genetically altering plants to prevent them from producing glycine betaine would be very beneficial to many agriculturally related industries.

To date, the gene coding for the enzyme responsible for oxidizing betaine aldehyde to glycine betaine, BADH, has been cloned and has been successfully expressed in transformed tobacco. In contrast, the gene encoding CMO is to date unknown and, accordingly, there has been no means to genetically engineer plants using the CMO gene. Since BADH and CMO are both required for glycine betaine production, the singular transformation of BADH without CMO is useless for increasing stress resistance, as glycine betaine is not produced. Also, when blocking of glycine betaine synthesis is desired it is more useful to block CMO than BADH. A block at the step catalyzed by BADH can cause accumulation of betaine aldehyde resulting from the oxidation of choline by CMO. This may inhibit plant growth and productivity because betaine aldehyde is a toxic metabolite and a structural analog of amino aldehyde intermediates of polyamine catabolism.

For the foregoing reasons, there is a need for a means to isolate a gene encoding a CMO-resemblant enzyme, and ideally to identify the sequence of a gene encoding a CMO-resemblant enzyme. As a corollary, there is a need for a purified CMO-resemblant enzyme. There is a need for a method to increase or decrease the glycine betaine concentration of plants. Still further, there is a need for a method to genetically engineer organisms to increase their resistance to stressful conditions.

SUMMARY OF THE INVENTION

The present invention is directed to a method of increasing the resistance of plants to harsh environmental conditions. Specifically exemplified is a method which involves the transformation of plants with a gene encoding a protein having choline monooxygenase activity. Although any method of transformation can be used, in a preferred embodiment of such a method, an *Agrobacterium tumefaciens* host cell is transformed with a vector containing a DNA sequence encoding choline monooxygenase and cultured; the cultured *A. tumefaciens* cell is then used to transform a plant cell according to procedures well known in the art. As a specific example to illustrate the teachings herein it is disclosed that tobacco, which does not express a CMO-type enzyme, has been successfully transformed through the procedures of the present invention, to display CMO activity. Transgenic tobacco expressing chimeric genes for BADH and CMO synthesizes glycine betaine. This aspect of the invention increases the transformed plant's resistance to stressful conditions by increasing the concentration of glycine betaine in tissues.

Another aspect of the present invention relates to an isolated DNA sequence encoding an enzyme having choline monooxygenase characteristics. An example of a DNA sequence according to the present invention is displayed in FIG. 2. Until now, a sequence encoding CMO has not been realized. This aspect of the invention provides, for the first time, sequences which can be used in genetic engineering for transformation and subsequent expression of proteins exhibiting CMO activity, thereby facilitating the biosynthesis of glycine betaine in plant tissues where it was previously absent.

An additional aspect of the present invention is directed toward a process for isolating DNA sequences for CMO-type enzymes. Disclosed herein is the isolation of a DNA sequence encoding a choline monooxygenase enzyme from spinach (*Spinacia oleracea*). This sequence provides a means to utilize known recombinant DNA techniques to isolate sequences encoding CMO enzymes in other species. For example, the DNA sequence disclosed herein, as well as fragments thereof, can be used as a probe to screen cDNA libraries of plants known to express a CMO-like enzyme. Such techniques are well known in the art and are routinely practiced with success.

Nucleotide sequences derived from FIG. 2 are yet another aspect of the invention as disclosed herein. "Derived from" is used herein to mean taken, obtained, received, traced, replicated, or descended from a source (chemical and/or biological). A derivative may be produced by chemical or biological manipulation (including but not limited to substitution, addition, insertion, deletion, extraction, isolation, mutation, and replication) of the original source, by means well known to those of ordinary skill in the art.

A further aspect of the invention relates to a plant made by the procedures disclosed herein. This aspect of the invention includes plants transformed with a DNA sequence which hybridizes to FIG. 2 under stringent conditions and which encodes a protein exhibiting CMO activity, as well as fragments of FIG. 2 sufficient to encode CMO activity. A preferred embodiment is a transgenic plant made through the procedures disclosed herein which displays CMO activity.

Still further, another aspect of the invention relates to a method of reducing the amount of glycine betaine in plants which normally produce it, and sequences which are antisense to CMO-encoding sequences, and thus which are useful in this method.

Yet another aspect of the invention is a method of increasing the choline content of a plant cell by inhibiting the conversion of choline into glycine betaine, as well as plant cells and plants affected by this method.

DESCRIPTION OF THE DRAWINGS

FIG. 2 depicts the nucleotide and deduced amino acid sequences of CMO cDNA clone pRS3. The amino acid sequences determined for tryptic peptides are underlined; overlaps between peptide sequences are underlined twice. The N-terminus of the processed polypeptide is indicated with an asterisk. The Cys-His pairs conserved in Rieske-type iron-sulfur proteins are marked with daggers. The stop codon and putative polyadenylation signal are boxed. The GenBank accession number for the nucleotide sequence shown is U85780.

FIG. 4 depicts the nucleotide sequence of the sugarbeet choline monooxygenase cDNA.

FIG. 5 depicts the deduced amino acid sequence of the sugarbeet choline monooxygenase cDNA.

BRIEF DESCRIPTION OF THE SEQUENCES

Figure 1:
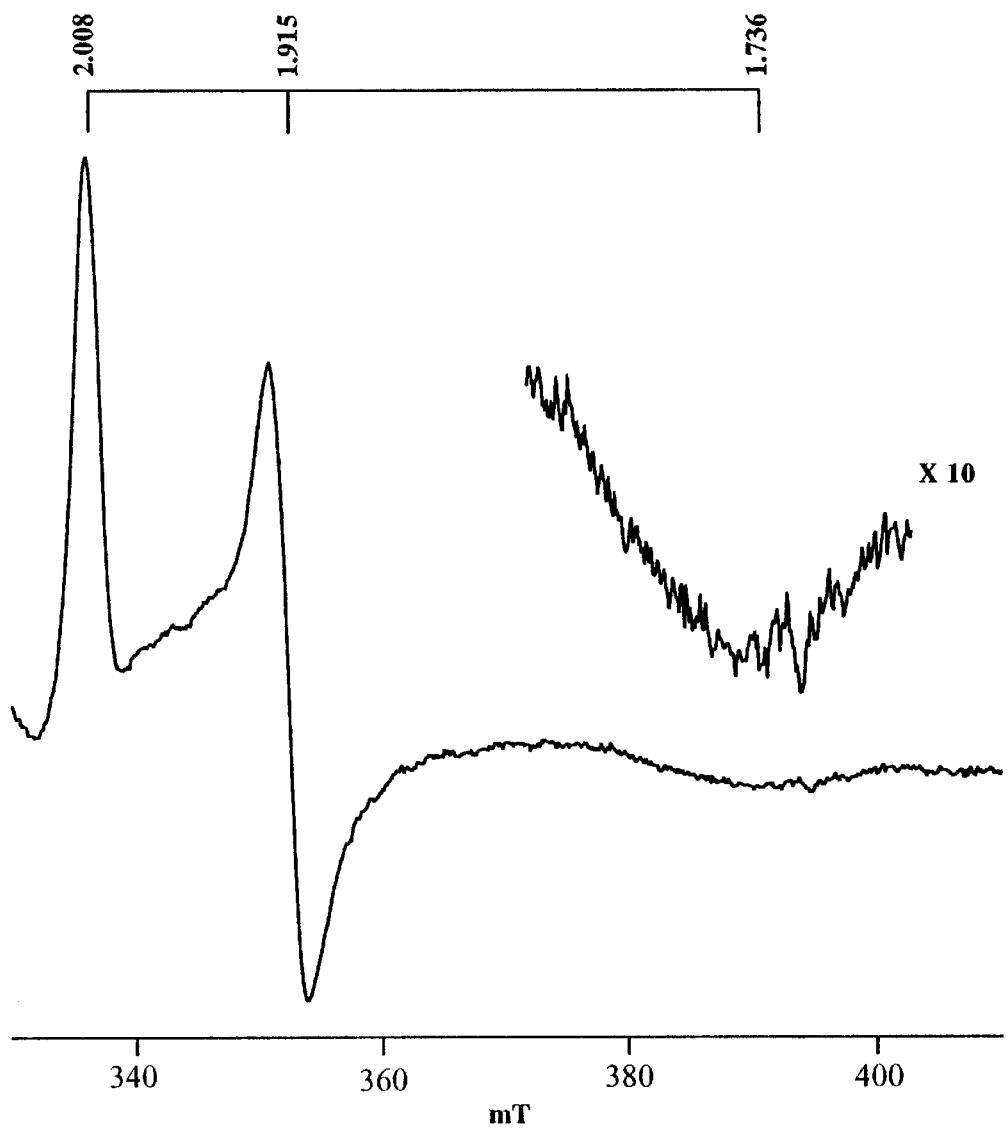
FIG. 1 is an EPR spectrum of CMO. Spectra of CMO reduced by sodium dithionite were acquired at 15K with a microwave power of 20 mW and a modulation amplitude of 10 G. The spectrum shown is the average of 16 measurements.

SEQ ID NO: 1 is a nucleotide sequence which encodes a spinach choline monooxygenase.

SEQ ID NO: 2 is the deduced amino acid sequence of the protein encoded by the nucleotide sequence of SEQ ID NO: 1.

SEQ ID NO: 3 is the nucleotide sequence of a sugarbeet choline monooxygenase.

SEQ ID NO: 4 is the deduced amino acid sequence of the protein encoded by the nucleotide sequence of SEQ ID NO: 3.

DETAILED DESCRIPTION OF THE INVENTION

The subject invention provides, for the first time, a sequence encoding choline monooxygenase or CMO, the enzyme which converts choline into betaine aldehyde, and a novel method for increasing the resistance of plants to stressful conditions. The nucleotide sequence of FIG. 2, representing the gene which encodes choline monooxygenase in spinach, is illustrative of a sequence encompassed by the subject invention. The disclosure of this CMO-encoding sequence provides the necessary component to bioengineer plants such that CMO-active enzymes can be produced by plants previously devoid of any CMO activity. This CMO encoding sequence, as well as sequences derived therefrom, also provides probes useful for the isolation and sequencing of genes encoding other related enzymes from other species through the use of widely known standard techniques.

Specifically exemplified herein is a method for producing a plant (previously devoid of CMO enzyme) which expresses a protein exhibiting CMO enzymatic activity. This exemplified method includes transforming an *Agrobacterium tumefaciens* cell with a vector containing the DNA sequence of FIG. 2, culturing the *A. tumefaciens* cell, and transforming a plant cell with the DNA sequence of FIG. 2.

Although plant transformation is exemplified herein by Agrobacterium mediated transformation, other known methods of transformation are encompassed by the subject invention. These include but are not limited to the following: direct gene transfer to protoplasts or cells using chemical or physical means such as polyethyleneglycol-mediated DNA uptake, biolistics, microinjection, electroporation, silicon carbide whiskers, agroinfection, viral vectors, liposome fusion, and liposome injection. Many commercially important crops lack an ability to accumulate glycine betaine, and therefore their stress tolerance may be improved by engineering of CMO and BADH. These crops include but are not limited to rice, corn, sorghum, tomato, potato, tobacco, lettuce, oilseed rape, and genotypes of citrus. In corn, single gene mutants lacking glycine betaine accumulation are known. The defect in these mutants was identified to be in the first step of choline oxidation i.e. that catalyzed by CMO (Rhodes and Rich, 1988; Lerma et al. 1991). In species such as rice both BADH and CMO need to be expressed to engineer glycine betaine synthesis (Rathinasabapathi et al. 1993). But corn mutants lacking glycine betaine may need to be transformed with CMO alone to engineer the synthesis of glycine betaine. The transformation of the crops listed above and many other crops of interest has become routine for the skilled artisan; and the polynucleotides of interest disclosed herein can be used in the transformation of these species according to known techniques to exhibit desired characteristics and otherwise accomplish the ends disclosed herein. Techniques for plant transformation are disclosed, for example, in Gartland and Davey (1995), Jones (1995) and Potrykus and Spangenberg (1995).

The nucleotide sequences disclosed herein can be modified by any of a variety of mutagenic techniques known in the art. Site-specific mutagenesis is a preferred method, using a series of mismatch polynucleotide primers for introducing nucleotide sequence variations at any desired locus within a gene or polynucleotide molecule. The exact sequence change produced by such means can be identified by nucleotide sequence determination in the region affected by the change. A modified gene or polynucleotide can be tested for functional effect of the modification by cloning the gene or polynucleotide in an expression vector, as disclosed herein, or using any other expression system known in the art, and expressing the modified gene in a transgenic microorganism or plant thereby.

Techniques for cloning, DNA isolation, modification, amplification, and purification, for enzymatic reactions involving DNA ligase, DNA polymerase, restriction endonucleases, and the like, and various separation techniques are known and commonly employed by those skilled in the art of genetic manipulation. A number of standard techniques are described in Old and Primrose (1981), Glover (ed.) (1985), Hames and Higgins (eds.) (1985), Sambrook et al. (1989), Innis et al. (eds.) (1990) and Harwood (1994) which are all incorporated by reference herein. Abbreviations, where employed, are those deemed standard in the field and commonly used in professional journals such as those cited herein.

Fragments of (a) the nucleotide sequence of FIG. 2, or (b) nucleotide sequences derived from FIG. 2, including sequences antisense to FIG. 2, which are useful according to the teachings herein can be produced by use of restriction enzymes or by limited digestion by Bal31 exonuclease. These polynucleotide fragments are then cloned into expression vectors with an appropriate selectable marker and ultimately transferred into plant cells according to the methods disclosed above. Plant cells transformed with these fragments are routinely cultured into callus, and/or regenerated into plants, which are then tested for the desired characteristics. In this manner, fragments of a nucleotide sequence of interest which are sufficient to confer the desired characteristics are routinely and predictably identified.

As is understood in the art, nucleotide mismatches can occur at the third or wobble base in a codon without causing amino acid substitutions in the final polypeptide sequence encoded thereby. Also, minor nucleotide modifications (e.g., substitutions, insertions, or deletions) in certain regions of a polynucleotide sequence can be tolerated and considered insignificant whenever such modifications result in changes in amino acid sequence that do not alter the functionality of the final product. It has been shown that chemically-synthesized copies of whole, or parts of, gene sequences can replace the corresponding regions in the natural gene without loss of gene function. Homologs of specific DNA sequences may be identified by those skilled in the art using the test of cross-hybridization of nucleic acids under conditions of stringency as is well understood in the art as described in Hames and Higgins (eds.) (1985). Thus, in this disclosure it will be understood by those of ordinary skill in the art that sequence variations can exist or purposely be designed into homologous sequences. Chemical synthesis of polynucleotides can be accomplished manually by using well-established procedures such as those disclosed by Carruthers (1983), or automated chemical synthesis can be performed using one of a number of commercially-available machines.

The subject invention also concerns polynucleotide molecules having sequences that are antisense to polynucleotides encoding CMO enzyme activity. Expression of an antisense polynucleotide molecule can block the production of the CMO-type protein. To be useful according to the teachings herein, an antisense polynucleotide molecule need only be of sufficient size to block the production of a protein exhibiting CMO-type activity. Such antisense polynucleotides can be constructed by techniques well known in the art and tested for usefulness by routinely determining their ability to block production of a protein exhibiting CMO-type activity according to the teachings herein. Introduction of a chimeric CMO gene with a sense polynucleotide molecule could also be employed to block the enzyme activity by cosuppression. The theory and practice behind the use of vectors with sense and antisense polynucleotide molecules to obtain transgenic plants with reduced levels of the target enzyme are well known in the art (Green et al., 1986; van der Krol et al., 1988; van der Krol et al., 1990a and b; Vaucheret et al., 1992). Reduction of glycine betaine level by blocking CMO can produce agronomically important genotypes in species that naturally accumulate glycine betaine such as wheat, barley, corn, sugarbeet, spinach, cotton, and sunflower. The benefits may include increased resistance to pests and pathogens; or ease of industrial processing, as in sugarbeet, where glycine betaine is an unwanted side product interfering with sugar crystallization. Methods to transform the above-listed species and many other crops are well-known to persons skilled in the art: for example, cotton (Umbeck et al., 1987), sunflower (Schoeffl and Baumann, 1985; Alibert et al., 1994), sugarbeet (Lindsey and Gallois, 1990; Hall et al., 1996) and corn (Fromm et al. ,1986), each of which is incorporated herein by reference.

It should be understood that the examples and embodiments described herein are for illustrative purposes only and that various modifications or changes in light thereof will be suggested to persons skilled in the art and are to be included within the spirit and purview of this application and the scope of the appended claims.

EXAMPLE 1

Protein Isolation and Analyses

Enzymatically active CMO was purified as described from leaves of spinach plants (*Spinacia oleracea* L. cv. Savoy Hybrid 612) that had been grown and salinized with 200 mM NaCl (Burnet et al., 1995). Non-heme iron (Atkin et al., 1973) and acid-labile sulfur (Beinert, 1983) were determined calorimetrically. Protein was assayed by the bicinchoninic acid method (Smith et al., 1985).

EXAMPLE 2

EPR Spectroscopy

Samples of purified CMO were adjusted to pH 10 with Glycine-KOH and reduced by adding 1 mg Na dithionite per 300 μL. They were analyzed using a Bruker ECS 106 EPR X-band spectrometer with ER 4116 DM resonator and an Oxford liquid helium cryostat. Temperature was controlled by an Oxford Intelligent controller, and monitored with a thermocouple 3 mm beneath the sample tube with liquid nitrogen as the reference. The microwave frequency was sampled by a Hewlett-Packard 5340A frequency counter. Data manipulations were carried out using the program IgorPro 2.04 (Wavemetrics, Lake Oswego, Oreg.).

EXAMPLE 3

Peptide Microsequencing

Purified CMO was subjected to SDS-PAGE and the $M_r \approx 45,000$ band was blotted to polyvinylidene difluoride membrane. Tryptic peptides were generated by the procedure of Fernandez et al. (1994) and purified by reverse-phase HPLC using an Aquapore RP-300(C-8, 2.1×220 mm) column developed with a trifluoroacetic acid-acetonitrile gradient. Isolated peptides were subjected to sequence analysis on an ABI Model 476A protein/peptide sequencer (Perkin-Elmer ABD). The N-terminal sequence of the intact protein was determined on a sample further purified by reverse-phase HPLC.

EXAMPLE 4 cDNA Cloning

Total RNA from salinized spinach leaves was extracted as described (Hall et al., 1978), except that a step to precipitate carbohydrates with 75 mM $BaCl_2$ was added. Poly $(A)^+$ RNA was isolated using Poly (U) Sephadex (Hondred et al., 1987), and used to construct a cDNA library ($9 \times 10^6$ pfu) in λ UniZap XR (Stratagene). A 532-bp DNA fragment was generated by reverse transcription (RT)-PCR with primers based on CMO peptides; the (+) and (−) primers were respectively 5'-CCIGA(A/G)CA(A/G)AA(T/C)(T/C)TNGA(C/T)CCIAA(A/G)G-3' (SEQ ID NO: 5) and 5'-CCATCAT(A/G)TT(C/T)TC(C/T)TC(T/G/A)AT(A/G)TA(A/G)TA(A/G)TC-3' (SEQ ID NO: 6). The RT-PCR reaction (100 μL) contained 3 ng first-strand cDNA, 40 pmol of each primer, 200 μM each of all four dNTPs, 50 mM KCl, 1.5 mM $MgCl_2$, 0.001 % (w/v) gelatin and 2.5 units of AmpliTaq DNA polymerase(Perkin-Elmer)in 10 mM Tris-HCl,pH 8.3. Forty cycles of 0.5 min each at 94° C. and 30° C. and 1 min at 50° C. were carried out. The 532-bp fragment was isolated from low-melting agarose (Sambrook et al., 1989), and labeled with [$-^{32}P$]dCTP ($>3 \times 10^9$ cpm/μg) by the random primer method. Library screening and in-vivo excision were according to the supplier's instructions. Screening the amplified library ($\approx 2 \times 10^5$ plaques) with this probe yielded 18 positive clones of which the largest was 1189 bp. The unamplified library ($\approx 2 \times 10^5$ plaques) was then screened with a 223-bp EcoRI fragment from the 5' region of this clone. Of eight positive clones, two having the longest inserts (pRS3 and pRS5) were sequenced in both strands using the fluorescent chain-terminating dideoxynucleotides method (Prober et al., 1987). They were identical except that pRS5 lacked 150 bp at the 5' end and had one base change in the 3' noncoding region. Sequences were analyzed with the Wisconsin GCG Sequence Analysis Package.

EXAMPLE 5

DNA and RNA Blot Analyses

Genomic DNA was prepared from leaves as described (Sambrook et al. 1989). Total RNA was isolated from control and salinized leaves (Puissant and Houdebine, 1990), denatured, and subjected to electrophoresis in formaldehyde/1.2% agarose gels (Sambrook et al., 1989). RNA was quantified by the orcinol method (Dawson et al., 1986). Blotting and hybridizations were performed using standard protocols (Sambrook et al., 1989). Molecular size markers were an RNA ladder (0.24–9.5 kb, GibcoBRL) for RNA blots, and HindIII-digested λ DNA fragments for DNA blots.

EXAMPLE 6

Antibody Production and Immunoblot Analysis

Rabbit antibodies were raised against CMO purified by SDS-PAGE and by reverse-phase HPLC, respectively. To determine the effect of salinization on CMO expression, spinach leaf proteins were precipitated with PEG 8000 (Burnet et al., 1995), separated by SDS-PAGE and transferred to nitrocellulose (Tokuhisa et aL, 1985). Prestained $M_r$ markers (BioRad) were run simultaneously. Blots were probed with a 1:500 dilution of rabbit serum (Tokuhisa et al., 1985).

EXAMPLE 7

Evidence for a Rieske-type [2Fe-2S] Center

Definitive evidence for an Fe—S center was sought by EPR spectroscopy and by chemical assays of acid-labile sulfide and non-heme iron. In EPR studies, upon reduction by sodium dithionite, a rhombic spectrum with apparent g values of 2.008, 1.915 and 1.736 was observed (FIG. 1). The narrow low field peak and broad high field trough resemble those reported for certain types of [2Fe-2S] cluster (Johnson, 1994). The $g_{avg}$ ($g_x$+$g_y$+$g_z$/3) of this spectrum was 1.89, similar to that of many 2 His-, 2 Cys-liganded Reiske-type [2Fe-2S] clusters (Mason et al., 1992). By contrast, [2Fe-2S] clusters liganded by 4 Cys residues typically have $g_{avg}$=1.94 (33). The spectrum for CMO reached maximum intensity at 15 K, somewhat lower than is typical of Rieske-type clusters, but still within the expected range. Consistent with these results, Fe and S analyses indicated that CMO contains approximately 2Fe and 2S per subunit (Table 1).

EXAMPLE 8 cDNA Cloning

Amino acid sequences were obtained for the N-terminus of CMO and for 12 tryptic peptides. Two internal sequences were used to design primers for RT-PCT, which gave a 532 bp-DNA. Screening a library with this fragment yielded several truncated CMO cDNAs; the 5' region from the longest of these was then used as a probe to isolate a full-length cDNA (FIG. 2). This cDNA (1622 bp) had 5' and 3' noncoding regions of 56 and 246 bp, respectively. A putative polyadenylation signal (AAATAAT) preceded the poly(A) sequence by 58 bp. The open reading frame (1320 bp) encoded 440 amino acids that included a 60-residue transit peptide. As the open reading frame begins with two adjacent ATG codons, either could be the translational start. However, the sequences flanking the second ATG match the consensus translational initiation motif in plants (Joshi, 1987). The coding region included all the amino acid sequences determined for purified CMO. The size and composition of the deduced transit peptide were typical for a chloroplast stromal targeting peptide (Cline et al., 1996), consistent with the stromal location of CMO (Brouquisse et al., 1989). The predicted $M_r$ of the processed polypeptide was 42,884. As this value differs from that obtained by MALDI-MS by less than the experimental error of the method, the CMO polypeptide is subject to very few if any post-translational modifications.

EXAMPLE 9

Primary Structure Comparisons

No sequence in the public data bases had close overall homology with CMO, so that no oxygenase of this kind is known to date. Rieske-type iron-sulfur proteins share a consensus sequence Cys-X-His (15 to 17 amino acids) Cys-X-X-His, where X=any amino acid. This motif, which is considered to be involved in binding the [2Fe-2S] cluster (Mason et al., 1992), was conserved in CMO (FIG. 2). This finding strongly supports the chemical and EPR data indicating that CMO has a [2Fe-2S] center. Besides this conserved motif, some local homologies were found with various bacterial oxygenases, particularly members of the benzene dioxygenase family (Harayama et al., 1992). Weak local homology was also found with bacterial alkyl group hydroxylases and with the Rieske iron-sulfur proteins of mitochondria and chloroplasts. Representative data for each of these three families are shown in Table 2. The presence of Rieske-type [2Fe-2S] cluster and the amino acid sequence of the protein, place CMO in a new class of plant oxygenases.

EXAMPLE 10

CMO Induction by Salinity

Figure 3A:
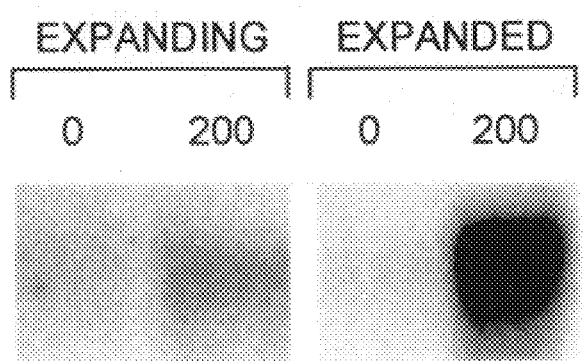
FIG. 3 depicts CMO expression in expanding and expanded spinach leaves. Plants had been irrigated with nutrient solution (0) or, for 10 days before the experiment, with nutrient solution containing 200 mM NaCl (200). (A) RNA blot analysis. Lanes contained 5 $\mu$g of total RNA. The probe was a 532-bp DNA fragment [positions 660–1191 of pRS3 (FIG. 2)]. Ethidium bromide staining demonstrated that all lanes contained equivalent amounts of RNA. Densitometry of autoradiographs indicated that salinization increased CMO mRNA levels by 2-fold in expanding leaves and 7-fold in expanded leaves. (B) Immunoblot analysis. Lanes contained 40 $\mu$g of total leaf protein. Rabbit antibodies against SDS-denatured CMO were used for immunodetection. (C) Extractable activity. CMO assayed in protein fractions following precipitation with polyethyleneglycol as described in Burnet et al.(1995). Bars are means of three determinations; the standard errors were less than 16% of the mean values.
Figure 3B:
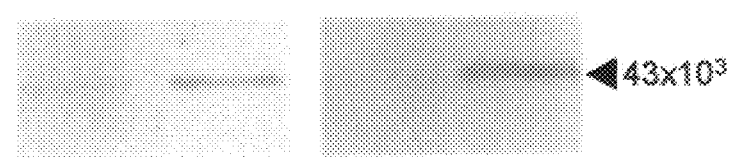
Figure 3C:
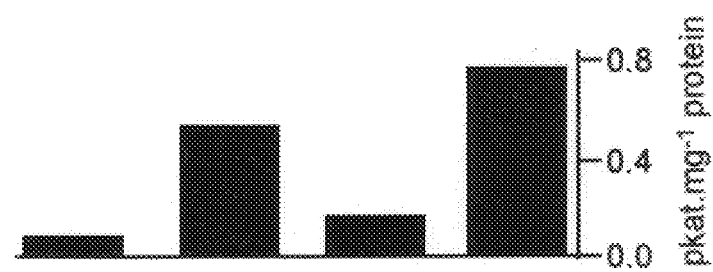

In unsalinized plants, CMO mRNA levels were low in both expanding and expanded leaves. Salinization increased these levels, especially in expanded leaves (FIG. 3A). CMO protein levels paralleled these changes (FIG. 3B). The rise in extractable CMO activity in salinized plants observed previously (Brouquisse et al., 1989) can therefore be attributed to an increase in CMO gene expression. The magnitudes of the salt-induced increases in CMO mRNA and protein are comparable to those reported for BADH (Rhodes et al., 1993).

EXAMPLE 11

Analysis of Genomic DNA

Following digestion of spinach genomic DNA with HindIII, EcoRV or EcoRI, blot analysis revealed single bands of about 18, 9 and 3.7 kb, respectively (not shown). This is consistent with there being one CMO gene containing a large intron(s). Reconstruction experiments also suggested a single copy of CMO per haploid genome (not shown).

EXAMPLE 12

Transformation of Tobacco

The plant expression vector pGACMO1 was constructed as follows: a SmaI-EcoRVDNA fragment containing all the CMO cDNA coding sequence was subcloned into HpaI site of pGA643 (An et al., 1988). The construct contained the following sequences between the pGA643 35S promoter and the cDNA: 15 bp of pBluescript vector sequence SmaI to EcoRI, 9 bp of sequences added to the CMO cDNA during cDNA cloning (CGGCACGAG), 21 bp of sequence from the pGA643's multiple cloning region. In this expression vector the insert sequence was flanked by Cauliflower mosaic virus 35S promoter at the 5' end and Agrobacterium Transcript 7's 3' untranslated region (158 bp) at the 3' end. Following introduction of the vector pGACMO1 into *Agrobacterium tumefaciens* LBA 4404, tobacco was transformed by the leaf disk method (Ebert et al. 1988). Transformants were selected for resistance to kanamycin sulfate (100 mg/L). The presence of CMO cDNA in the transgenic plants were verified by using the polymerase chain reaction to amplify a fragment of CMO cDNA from genomic DNA isolated from leaves.

EXAMPLE 13

Expression of CMO in Transgenic Tobacco

Total RNA was isolated from leaves of wild-type Wisconsin 38, vector alone control and fourteen plants positive for CMO cDNA by PCR screening. These RNA samples (10 to 30 μg per lane) were separated on a formaldehyde agarose gel and blotted. RNA blots were probed with spinach CMO cDNA (AccI—EcoRV fragment). Vector alone control and wild-type tobacco did not have any signal, but ten CMO transgenic tobacco had a single band that corresponded in intensity to about 50 to 100% of that of salinized spinach. The message size expressed in transgenic tobacco was as expected (about 1.8 to 1.9 kbp) (data not shown). Protein extracts were made from young fully-expanded leaves of tobacco (wild-type, vector control, and transgenic tobacco expressing CMO mRNA). Partially purified protein fractions (PEG precipitation and molecular size exclusion chromatography) were used in a protein blot and probed with rabbit antibody raised against purified spinach CMO. In these blots, the controls (wild-type and vector control) lacked a positive signal and samples from CMO positive plants had a band at the expected subunit size (about 45 kDa). The intensity of the CMO band was comparable to about 2% of salinized spinach (data not shown).

The transgenic tobacco expressing CMO cDNA has only CMO but does not have spinach betaine aldehyde dehydrogenase (BADH). However, wild-type tobacco has a weak but detectable BADH activity (Rathinasabapathi et al., 994). Hence it was expected that tobacco transformed with spinach CMO alone would synthesize glycinebetaine. Glycine betaine levels in vector-alone controls, wild-type tobacco, and CMO positive transgenic tobacco were measured using fast atom bombardment mass spectrometry (Rhodes and Hanson, 1993, incorporated herein by reference). Wild-type tobacco or tobacco transformed with vector alone contained small quantities of glycine betaine (i.e about 75 nmoles per g dry wt.). The transgenic tobacco expressing CMO had 2 to 4× higher glycine betaine levels indicating that spinach CMO is functionally expressed in transgenic tobacco plants (Table 3). Glycine betaine synthesis in transgenic tobacco transformed with spinach CMO cDNA indicates that spinach cDNA for CMO introduced into tobacco is sufficient to express a functional CMO enzyme. Additionally, constitutive expression of spinach CMO in tobacco did not have any deleterious effects on plant growth and development.

EXAMPLE 14

Testing Transgenic Tobacco for Stress Tolerance

Transgenic tobacco constitutively expressing spinach CMO, wild-type, and the vector alone control plants were grown in large pots under greenhouse conditions promoting realistic evaporative demands. Plants about six weeks old were salinized to various levels by step-wise increase of salinity ($Na^+/Ca^{2+}$ ratio 5.7:1) to final level to 250 mM and held for several weeks prior to harvest. The stress tolerance of these plants was assessed by measuring growth (fresh weight changes) and water status (solute potential; data not shown) using standard techniques known in the art. Results shown in Table 4 on shoot fresh weight at harvest indicate that two (235-3 and 231-23) of three plants expressing spinach CMO had increased their shoot biomass significantly over the controls under both control and salinity stress. These results show that the transgene conferred a growth advantage over the control in stressful conditions.

EXAMPLE 15

Isolation of Sugar Beet CMO cDNA and its use in Beet Transformation

Total RNA from salinized sugarbeet leaves was extracted as described (Hall et al., 1978), except that a step to precipitate carbohydrates with 75 mM $BaCl_2$ was added. Poly $(A)^+$ RNA was isolated using Poly (U) Sephadex (Hondred et al., 1987), and used to construct a cDNA library in λ UniZap XR (Stratagene). A spinach cDNA fragment including most of the coding region was isolated from low-melting agarose (Sambrook et al., 1989), and labeled with [ $-^{32}P$]dCTP ($>3\times10^9$ cpm/μg) by the random primer method. Following library screening, clones having the longest inserts were sequenced in both strands using the fluorescent chain-terminating dideoxynucleotides method (Prober et al., 1987). Sequences were analyzed with the Wisconsin GCG Sequence Analysis Package. Two clones thus isolated represented a full length cDNA of 1751 bp that encodes a polypeptide of 446 amino acids and has a 377-bp 3'-untranslated region. The deduced beet CMO amino acid sequence comprised a transit peptide and a 381-residue mature peptide that was 84% identical (97% similar) to that of spinach and that showed the same consensus motif for coordinating a Rieske-type [2Fe-2S] cluster. As in spinach CMO, a mononuclear Fe-binding motif (Jiang et al., 1996) was also present. The GenBank accession number for the composite beet CMO nucleotide sequence is AF 023132 (FIG. 4).

Sugarbeet CMO cDNA in pBluescript is subcloned into a binary expression vector such as pGA643 (An et al.,1988) in antisense orientation. The binary vector is then mobilized into Agrobacterium tumefaciens LBA4404 by triparental mating (An et al.,1 988). Transformed agrobacterium is selected for streptomycin, kanamycin and tetracyclin resistance. Sugarbeet cultivar Kwerta is propagated in vitro as shoot cultures in MS medium (Murashigc & Skoog, 1962) supplemented with 30 g/l sucrose and 0.25 mg/l BAP (Lindsey and Gallois, 1990), under continuous light.

For transformation, shoot base explants (about 1 cm×1 cm×2 cm) are derived from the axenic shoot cultures. The explants are incubated in a suspension of agrobacterium ($2.5-5\times10^8$ cells/ml) for 24 h and then cultured on selection medium (MS medium supplemented with BAP 1 mg/l, carbenicillin 200 mg/l, kanamycin 100 mg/l and 5 mM glycine betaine). The tissue slices are transferred to fresh selection medium every fifteen days. Putative transgenic shoots identified by kanamycin-resistanceare then transferred to rooting medium (MS medium supplemented with NAA 5 mg/l).

The levels of CMO mRNA in vector-alone controls and antisense CMO transformants are compared by RNA blot analysis of plants under control and salt-stressed (300 mM NaCl) conditions. CMO activity is measured in leaf extracts using the radiometric assay described previously (Burnet et al., 1995, incorporated herein by reference). CMO protein in transgenic plants is analyzed by immunoblotting using CMO-specific antibodies. Glycine betaine levels in various tissues of vector-alone controls and antisense CMO transgenic beet are determined using fast atom bombardment mass spectrometry(Rhodes and Hanson, 1993).

Antisense CMO beet transformants containing low glycine betaine levels are compared with vector alone control plants for salinity tolerance, growth traits, and storage root sugar level in plants grown under controlled conditions. Differential damage of these transformants by specific insect pests and diseases is evaluated in a multilocation field trial. The plants are cultivated under a standard pest management protocol. The severity of incidence of pests and diseases on the transgenic plants is scored in four different locations using a scale of 1–10 estimated for each pest or disease.

TABLE 1

| Non-heme iron and acid-labile sulfur content of CMO | |
| --- | --- |
| Analyte | nmol $mL^{-1}$ |
| CMO subunit | 57 (0.3) |
| Fe | 100 (5.0) |
| S | 99 (6.0) |

Enzymatically active CMO was prepared as described (Burnet et al., 1995). The reverse-phase HPLC elution profile (absorbance at 280 nm) of the preparation indicated that CMO was 51% of the total protein. This value, together with a $M_r$ of 43,026 was used to calculate the molar concentration of CMO subunit. Values are means and SE (in parentheses) for 3 or 4 determinations.

TABLE 2

Amino acid sequence homology between CMO and other proteins with Rieske-type iron-sulfur centers

| Sequence Similarity | Species | Size of region compared (residues) | % Identity | % |
|---|---|---|---|---|
| Mitochondrial Rieske Fe-S protein 36.1 | Zea mays | 72 | 29.2 | |
| Naphthalene dioxygenase .0 | Pseudomonas putida | 195 | 29.2 | 43 |
| Vanillate demethylase 43.0 | Pseudomonas sp. | 58 | 31.0 | |

The data shown are for representative members of families. The regions of homology that were compared included the conserved [2Fe-2S] cluster binding motif. Local homologies were first identified using BLASTP with non-redundant sequences in the NCBI database and individual entries were compared by FASTA.

Table 3. Glycine betaine levels measured in young fully-expanded leaves of wild-type tobacco Wisconsin 38, vector control and three transgenic tobacco expressing spinach CMO. Transgenic plants were primary transformants. The replicates were generated by micropropagation. All plants were grown under identical non-stress conditions. The values are means and standard errors for three independent samples. *=significantly different from controls at p=0.05.

| Genotype | | Glycine betaine (nmol$^{-1}$ .g dry wt.) |
|---|---|---|
| Wild-type Wisconsin 38 | | 62 ± 10 |
| pGA vector control | | 88 ± 10 |
| 231-23 | CMO transgenic 1 | 169 ± 28* |
| 235-3 | CMO transgenic 2 | 270 ± 51* |
| 231-14 | CMO transgenic 3 | 293 ± 68* |

Table 4. Growth of wild-type tobacco Wisconsin 38, vector control and three transgenic tobacco plants expressing spinach CMO, under control conditions and salinity stress. Control plants were irrigated with nutrient solution and salt stressed plants with nutrient solution containing salts increasing in steps of 50 mM every three days up to 150 mM at which concentration the treated plants were held for 3 weeks. Transgenic plants were primary transformants. The replicates were generated by micropropagation. Final fresh weight of shoots is reported. The values are means and standard errors for four plants (Nuccio, M., Russell, B., Nolte, K., Rathinasabapathi, B and A. D. Hanson, unpublished results). a–d Means followed by different letters are statistically significant at p=0.05.

| Genotype | | Shoot Fresh weight (g per plant) | |
|---|---|---|---|
| | | Control | Salinized |
| pGA vector control | | 379$^a$ ± 41 | 195$^c$ ± 15 |
| Wisconsin 38 | | 384$^a$ ± 21 | 193$^c$ ± 22 |
| 231-23 | CMO transgenic 1 | 459$^b$ ± 27 | 235$^d$ ± 28 |
| 235-3 | CMO transgenic 2 | 478$^b$ ± 42 | 256$^d$ ± 12 |
| 231-14 | CMO transgenic 3 | 418$^b$ ± 41 | 222$^c$ ± 40 |

References

Alibert, G, C. Aslane-Chanabe and M. Burrus (1994) *Plant Physiol. Biochem*.32:31–44.

Atkin, C. L., L. Thelander and P. Reichard (1973) *J. Biol. Chem.* 248:7464–7472.

Beinert, H. (1983) *Anal. Biochem.* 131:373–378.

Brinkmann, H. and W. Martin (1995) *Plant Mol. Biol.* 30:65–75.

Brouquisse, R. P. Weigel, D. Rhodes, C. F. Yocum and A. D. Hanson (1989) *Plant Physiol.* 90:322–329.

Burnet, M., P. J. Lafontaine and A. D. Hanson (1995) *Plant Physiol.* 108:581–588.

Carruthers (1983) *Methodology of DNA and RNA Sequencing*, Chapt. 1, Weissman (ed.), Praeger Publishers New York.

Cline, K. and R. Henry (1996) *Annu. Rev. Cell Dev. Biol.* 12:1–26.

Corcuera, L. J. (1993) *Phytochem* 33:741–747.

Dawson, R. M. C., D. C. Elliott, W. H. Elliott and K. M. Jones (1986) *Data for Biochemical Research* (Clarendon Press, Oxford), 3rd Ed., pp. 543–544.

Ebert et al. [1988] *Plant Mol. Biol. Manual* A3, (Kluwer, Dordrecht) 1–19).

Fernandez, J., L. Andrews and S. M. Mische (1994) *In Techniques in Protein Chemistry*, ed. Crabb, J. S. (Academic Press, New York), 5th Ed.

Fromm, M., L. P. Taylor and V. Walbot (1986) *Nature* 319:791–793.

Gartland, K. M. A. and M. R. Davey (1995) eds. *Agrobacterium Protocols*. (Humana Press, Totowa, N.J.).

Gorham, J. (1995) *In Amino Acids and Their Derivatives in Higher Plants*, ed. Wallsgrove, R. M. (Cambridge University Press, Cambridge), pp. 173–203.

Green, P. J., O. Pines and M. Inouye (1986) *Annu. Rev. Biochem.* 55:569–597.

Hall, T. C., Y. Ma, B. U. Buchbinder, J. W. Pyne, S. M. Sun and F. A. Bliss (1978) *Proc. Natl. Acad. Sci. USA* 75:3190–3200.

Hall R. D, T. Riksen-Bruinsma, G. J. Weyens, I. J. Rosquin, P. N. Denys, I. J. Evans, J. E. Lathouwers, M. P. Lefebvre, J. M. Dunwell, A. Tunen and F. A. Krens (1996) *Bio/Technol.* 14:1133–1138.

Hames, B. D and S. J. Higgins (1985) *Nucleic acid hybridization:A practical approach*. (IRL press, Oxford).

Hanson, A. D. and W. D. Hitz (1982) *Annu. Rev. Plant Physiol.* 33:163–203.

Hanson, A. D and D. Rhodes (1983) *Plant Physiol.* 71:692–700.

Harayama, S., M. Kok and E. L. Neidle (1992) *Annu. Rev. Microbiol.* 46:565–601.

Harwood, A. J. (1994) ed. *Protocols for gene analysis* (Humana Press, Totowa, N.J.)

Hayashi, H., Alia, L. Mustardy, P. Deshnium, M. Ida and N. Murata (1997) *The Plant J.* 12:133–142.

Hondred, D., D-W. Wadle, D. E. Titus and W. M. Becker (1987) *Plant Mol. Biol.* 9:259–275.

Innis, M. A., D. H. Gelfand, J. J. Sninsky and T. J. White (1990) eds. *PCR protocols: A guide to methods and applications*. (Academic Press, San Diego).

Ishitani, M., T. Nakamura, S. Y. Han and T. Takabe (1995) *Plant Mol. Biol.* 27:307–315.
Jiang, H., Parales, R. E., Lynch, N. A., Gibson, D. T. (1996) *J Bacteriol* 178:3133–3139.
Johnson, M. K. (1994) In *Encyclopedia of Inorganic Chemistry*, ed. King, R. B. (Wiley, N.Y.), Vol. 4, pp. 1896–1915.
Jones H. (1995) Ed. *Plant Gene transfer and expression protocols*, (Humana Press, Totowa, N.J.).
Joshi, C. P. (1987) *Nucl. Acids Res.* 15:6643–6653.
Kishor, P. B. K., Z. Hong, G. Miao, C. Hu and D. P. S. Verma (1995) *Plant Physiol.* 108:1387–1394.
Landfald, B. and A. R. Strom (1986) *J. Bacteriol.* 165:849–855.
Lerma, C., P. J.Rich, G. C. Ju, W. J. Yang, A. D. Hanson and D. Rhodes (1991) *Plant Physiol* 95:1113–1119.
LeRudulier, D., A. R. Strom, A. M. Dandekar, L. T. Smith and R. C. Valentine (1984) *Science* 224:1064–1068.
Lilius, G., N. Holmberg and L. Bulow (1996) *Bio/Technology* 14:177–180.
Lindsey, K. and P. Gallois (1990) *J Exp. Bot.*41:529–536.
Makay, M. A., R. S. Norton and L. J. Borowizka (1984) *J Gen. Microbiol.* 130:2177–2191.
Mason, J. R. and R. Cammack (1992) *Annu. Rev. Microbiol.* 46:277–305.
McCue, K. F. and A. D. Hanson (1990) *Trends Biotech.* 8:358–362.
McCue, K. F. and A. D. Hanson (1992) *Plant Mol. Biol.* 18:1–11.
Murashige, T and F. Skoog (1962) *Physiol. Plant.* 15:473–497.
Nagasawa, T. N. Mori, Y. Tani and K. Ogata (1976) *Agric. Biol Chem.* 40:2077–2084.
Nomura, M., M. Ishitani, T. Takabe, A. K. Rai and T. Takabe (1995) *Plant Physiol.* 107:703–708.
Nuccio, M., B. L. Russell, B. Rathinasabapathi and A. D. Hanson (1997) Unpublished results.
Old, R. W and S. B. Primrose (1985) *Principles of Gene Manipulation*. (Blackwell Scientific, Oxford) 3rd ed.
Papageorgiou, G. C. and N. Murata (1995) *Photosynthesis Res.* 44:243–252.
Pearce, R. B., R. N.Strange and H.Smith (1976) *Phytochem.* 15:953–954.
Potrykus, I. and G. Spangenberg (1995) eds.*Gene transfer to plants*, (Springer, N.Y.).
Prober, J. M., G. L. Trainor, R. J. Dam, F. W. Hobbs, C. W. Robertson, R. J. Zagursky, A. J. Cocuzza, M. A. Jensen and K. Baumeister (1987) *Science* 238:336–341.
Puissant, C. and L.-M. Houdebine (1990) *BioTechniques* 8:148–149.
Rathinasabapathi,B., M. Burnett, B. L. Russell, D. A. Gage, P. Liao, G. J. Nye, P. Scott, J. H. Golbeck and A. D. Hanson (1997) *Proc. Natl. Acad. Sci. USA* 94:3454–3458.
Rathinasabapathi, B., D. A. Gage, D. J. Mackill and A. D. Hanson (1993) *Crop Sci.* 33:534–538.
Rathinasabapathi, B., K. F. McCue, D. A. Gage and A. D. Hanson (1994) *Planta* 193:155–162.
Rhodes, D and P.J. Rich (1988) *Plant Physiol.*88:102–108.
Rhodes, D and A. D. Hanson (1993) *Annu. Rev. Plant Physiol. Plant Mol. Biol.* 44:357–384.
Rozwadowski, K. L., Khachatourians, G. G. and Selvaraj, G. (1991) *J. Bacteriol.* 173:472–478.
Russell, B. L., B. Rathinasabapathi and A. D. Hanson (1997) *Plant Physiol.* (In press).
Sambrook, J., E. F. Fritsch and T. Maruatis (1989) *Molecular cloning: A Laboratory Manual* (Cold Spring Harbor Lab. Press, Plainview, N.Y.), 2nd Ed.
Schoeffl, F. and G. Baumann (1985) *EMBO J.*4:1119–1124.
Smith, P. K., R. I. Krohn, G. T. Hermanson, A. K. Mallia, F. H. Gartner, M. D. Provenzano, E. K. Fujimoto, N. M. Goeke, B. J. Olson and D. C. Klenk (1985) *Anal. Biochem.* 150:76–85.
Tarczynski, M. C., R. G. Jensen and H. J. Bohnert (1993) *Science* 259:508–510.
Tokuhisa, J. G., S. M. Daniels and P. H. Quail (1985) *Planta* 164:321–332.
Tsuge, H., Y. Nakano, H. Onishi, Y. Futamura and K. Ohashi (1980) *Biochem. Biophys. Acta* 614:274–284.
Umbeck, P., G. Johnson, K. Barton and W. Swain (1987) *Biotechnol.*5:263–266.
Van der Krol, A. R., L. A. Mur, M. Beld, J. N. M. Mol and A. R.Stuitje (1990a) *Plant Cell* 2:291–299.
Van der Krol, A. R., L. A. Mur, P. De Lange, J. N. M. Mol and A. R.Stuitje(1990b) *Plant Mol Biol* 14:457–466.
Van der Krol, A. R., P. E. Lenting, J. Veenstra, I. M. van der Meer, R. E. Koes and A. G. M. Gerats (1998) *Nature* 333:866–869.
Vaucheret, H., J. Kronenberger, A. Lepingle,F. Vilaine,J. P. Boutin and M. Caboche (1992) *Plant J.* 2:559–569.
Warr, S. R. C., R. H. Reed and W D P Stewart (1998) *Plant Cell Environ* 11:137–142.
Yancey, P. H. (1994) In *Cellular and Molecular Physiology of Cell Volume Regulation*, Stange, K. (CRC Press, Boca Raton), pp. 81–109.

We claim:

1. An isolated polynucleotide molecule that encodes a protein exhibiting choline monooxygenase (CMO) activity, said polynucleotide molecule being capable of hybridizing to a polynucleotide comprising the sequence of SEQ ID NO: 1 under high stringency conditions.

2. The polynucleotide of claim 1 having the nucleotide sequence of SEQ ID NO: 1.

3. An expression vector comprising the polynucleotide molecule of claim 1.

4. A process for increasing the resistance of plants to stressful conditions comprising incorporating the polynucleotide molecule of claim 1 into the genome of said plant under conditions whereby said polynucleotide is expressed, whereby said plant produces glycine betaine.

5. A plant produced by the method of claim 4, or descendants of said plant.

6. The method of claim 4 wherein said plant is tobacco.
7. A plant of claim 5, wherein said plant is tobacco.
8. The method of claim 4, wherein said plant is wheat.
9. A plant of claim 5, wherein said plant is wheat.
10. The method of claim 4 wherein said plant is barley.
11. A plant of claim 5, wherein said plant is barley.
12. The method of claim 4 wherein said plant is corn.
13. A plant of claim 5, wherein said plant is corn.
14. The method of claim 4 wherein said plant is sugarcane.
15. A plant of claim 5, wherein said plant is sugarcane.
16. The method of claim 4 wherein said plant is sugar beet.
17. A plant of claim 5, wherein said plant is sugar beet.
18. The method of claim 4 wherein said plant is spinach.
19. A plant of claim 5, wherein said plant is spinach.
20. The method of claim 4 wherein said plant is cotton.
21. A plant of claim 5, wherein said plant is cotton.
22. The method of claim 4 wherein said plant is sunflower.
23. A plant of claim 5, wherein said plant is sunflower.
24. The method of claim 4 wherein said plant is rice.
25. A plant of claim 5, wherein said plant is rice.
26. The method of claim 4 wherein said plant is sorghum.
27. A plant of claim 5, wherein said plant is sorghum.
28. The method of claim 4 wherein said plant is tomato.
29. A plant of claim 5, wherein said plant is tomato.
30. The method of claim 4 wherein said plant is potato.
31. A plant of claim 5, wherein said plant is potato.
32. The method of claim 4 wherein said plant is lettuce.
33. A plant of claim 5, wherein said plant is lettuce.
34. The method of claim 4 wherein said plant is oilseed rape.
35. A plant of claim 5, wherein said plant is oilseed rape.
36. The method of claim 4 wherein said plant is a genotype of citrus.
37. A plant of claim 5, wherein said plant is a genotype of citrus.
38. Seed of the plant of claim 5.
39. A method of decreasing the production of glycine betaine in a plant comprising incorporating the polynucleotide molecule of claim 1 in antisense form into the genome of said plant under conditions whereby said antisense polynucleotide is expressed, whereby said plant produces no or less glycine betaine.
40. A plant produced by the method of claim 39, or descendants of said plant.
41. Seed of the plant of claim 40.
42. The method of claim 39, wherein said plant is sugar beet.
43. A plant of claim 40, wherein said plant is sugar beet.
44. An isolated polynucleotide molecule that encodes a protein exhibiting choline monotygenase (CMO) sequence of SEQ ID NO: 3 activity, said polynucleotide molecule being capable of hybridizing to a polynucleotide having the sequence of SEQ ID NO: 3 under high stringency conditions.
45. A plant comprising cells which comprise the polynucleotide of claim 1, wherein said polynucleotide is not native to said cells and wherein said polynucleotide is expressed to produce a protein exhibiting CMO activity.
46. A plant comprising cells which comprise the polynucleotide of claim 44, wherein said polynucleotideis not native to said cells and wherein said polynucleotide is expressed to produce a protein exhibiting CMO activity.
47. Seed of the plant of claim 45, said seed comprising said polynucleotide.
48. Seed of the plant of claim 46, said seed comprising said polynucleotide.

* * * * *

UNITED STATES PATENT AND TRADEMARK OFFICE
CERTIFICATE OF CORRECTION

PATENT NO. : 6,310,271 B1
DATED : October 30, 2001
INVENTOR(S) : Andrew D. Hanson, Bala Rathinasabapathi and Michael Burnet It is certified that error appears in the above-identified patent and that said Letters Patent is hereby corrected as shown below:

Column 4,
Line 63, should read -- SEQ ID NO: 5 is a primer used in accord with the teachings herein. --
Line 64, should read -- SEQ ID NO: 6 is a primer used in accord with the teachings herein. --

Column 7,
Line 14, "(Fromm et al. ,1986)" should read -- (Fromm *et al.*, 1986) --.

Column 8,
Line 18, "[ -$^{32}$P]" should read -- [$\propto$-$^{32}$P] --;
Line 57, "et aL, 1985" should read -- et al., 1985 --.

Column 9,
Line 29, "ATG match thc" should read -- ATG match the --.

Column 11,
Line 7, "et al., 994)." should read -- *et al.*, 1994). --;
Line 33, "step-wise increase" should read -- stepwise increase --;
Line 59, "[ -$^{32}$P]" should read -- [$\propto$-$^{32}$P] --;

Column 12,
Line 13, "(An et al., 1 988)." should read -- (An *et al.*, 1988) --.
Line 16, "Murashigc" should read -- Murashige --.

Column 15,
Line 33, "Biol" should read -- Biol. --.

Column 16,
Line 40, "(1998)" should read -- (1988) --;
Line 44, "(1998)" should read -- (1988) --.

Column 25,
Line 22, "comprising" should read -- having --;
Line 28, "ofplants" should read -- of plants --.

UNITED STATES PATENT AND TRADEMARK OFFICE
CERTIFICATE OF CORRECTION

PATENT NO. : 6,310,271 B1
DATED : October 30, 2001
INVENTOR(S) : Andrew D. Hanson, Bala Rathinasabapathi and Michael Burnet It is certified that error appears in the above-identified patent and that said Letters Patent is hereby corrected as shown below:

Column 26,
Lines 43-44, "exhibiting choline monotygenase (CMO) sequence of SEQ ID NO: 3 activity" should read -- exhibiting CMO activity --;
Line 53, "polynucleotideis" should read -- polynucleotide is --.

Signed and Sealed this

Twenty-fourth Day of September, 2002

Attest:

JAMES E. ROGAN
Attesting Officer
Director of the United States Patent and Trademark Office

SEQUENCE LISTING

```
<160> NUMBER OF SEQ ID NOS:  6

<210> SEQ ID NO 1
<211> LENGTH: 1622
<212> TYPE: DNA
<213> ORGANISM: Spinacia oleracea

<400> SEQUENCE: 1
tagtaagggt gtagctaatt agcaaaataa acaaaaagga agtgttgagt tggttaatga        60
tggcagcaag cgcaagcgca accacaatgt tgctaaaata cccaactaca gtttgtggta       120
ttccaaatcc ttcatcaaac aataataatg atccttcaaa caatatagtt tctattccac       180
```

-continued

```
aaaatactac taatccaaca cttaagtccc gtacacctaa taaaatcacc accaacgccg    240
tcgcggcacc gtcctttcct tctttaacca ccactacacc gtcgtccatc caatcacttg    300
tccacgaatt cgaccctcaa attccccctg aagacgctca tacacctcct agctcttggt    360
ataccgaacc tgccttctat tcccatgaac ttgagcgtat ctttatataaa ggatggcaag    420 ttgcagggat cagcgatcaa ataaaagagc ctaaccaata tttcactggc agcttaggaa    480
atgttgaata tttggtgtct cgagatggtg aagggaaagt tcatgcattt cacaatgttt    540
gcacccatcg tgcatctatt cttgcttgcg gtagtggcaa aaagtcgtgt ttcgtgtgcc    600
cttaccatgg atgggtatat ggcatggacg gatcacttgc gaaagcctcc aaagcaaaac    660
ctgaacaaaa cttggatcct aaagaacttg ggcttgtacc cctaaaagtt gcagtatggg    720
ggccgttcgt tcttatcagc ttggacagat cacttgaaga aggtggtgat gttggaactg    780
agtggcttgg tacttctgct gaagatgtta aggcccatgc ttttgatcct tcacttcaat    840
tcattcacag aagtgaattc ccaatggaat ctaattggaa gattttcagt gacaactact    900
tggatagctc atatcatgtt ccttatgcac acaaatacta tgcaactgaa ctcaactttg    960
acacttacga tacccaaatg atcgaaaacg ttacaattca aagagtggaa ggaagttcaa   1020
acaagcctga tggttttgat agagttggaa ttcaagcatt ctatgctttc gcgtatccaa   1080
atttcgctgt ggaaaggtat ggcccttgga tgactacaat gcatattcac ccattaggac   1140
caaggaaatg caaactagtg gtggactatt atattgaaaa ttctatgttg gatgacaagg   1200
attacatcga agggcata gcaatcaatg ataacgtaca gagggaagat gtggtgctgt   1260
gtgaaagtgt acaagaggt ttggagacac cagcatatcg tagtgggaga tatgtgatgc   1320
ctattgagaa aggaatccac catttccact gctggttgca acaaactttg aagtaattgt   1380
tgacttgact tcaccggacg tttgcgtgct cctcttggct cttgcagtta gttatgtgtg   1440
tatgctcatg gcctaaactt ataacatttt atactcaatt tataataaac accatagtaa   1500
gtacctcaga tatcccgtgc attttcattt tcagggaaa taatgacatt gtctatcaat   1560
atcaatatca atatcaatat caatattacc agtaatttta aacaaaaaaa aaaaaaaaa   1620 aa                                                                  1622
```

<210> SEQ ID NO 2
<211> LENGTH: 439
<212> TYPE: PRT
<213> ORGANISM: Spinacia oleracea

<400> SEQUENCE: 2

```
Met Met Ala Ala Ser Ala Ser Ala Thr Thr Met Leu Leu Lys Tyr Pro
 1               5                  10                  15

Thr Thr Val Cys Gly Ile Pro Asn Pro Ser Asn Asn Asn Asn Asp
            20                  25                  30

Pro Ser Asn Asn Ile Val Ser Ile Pro Gln Asn Thr Thr Asn Pro Thr
        35                  40                  45

Leu Lys Ser Arg Thr Pro Asn Lys Ile Thr Thr Asn Ala Val Ala Ala
    50                  55                  60

Pro Ser Phe Pro Ser Leu Thr Thr Thr Pro Ser Ser Ile Gln Ser
65                  70                  75                  80

Leu Val His Glu Phe Asp Pro Gln Ile Pro Pro Glu Asp Ala His Thr
                85                  90                  95

Pro Pro Ser Ser Trp Tyr Thr Glu Pro Ala Phe Tyr Ser His Glu Leu
            100                 105                 110
```

Glu Arg Ile Phe Tyr Lys Gly Trp Gln Val Ala Gly Ile Ser Asp Gln
            115                 120                 125

Ile Lys Glu Pro Asn Gln Tyr Phe Thr Gly Ser Leu Gly Asn Val Glu
    130                 135                 140

Tyr Leu Val Ser Arg Asp Gly Glu Gly Lys Val His Ala Phe His Asn
145                 150                 155                 160

Val Cys Thr His Arg Ala Ser Ile Leu Ala Cys Gly Ser Gly Lys Lys
                165                 170                 175

Ser Cys Phe Val Cys Pro Tyr His Gly Trp Val Tyr Gly Met Asp Gly
                180                 185                 190

Ser Leu Ala Lys Ala Ser Lys Ala Lys Pro Glu Gln Asn Leu Asp Pro
            195                 200                 205

Lys Glu Leu Gly Leu Val Pro Leu Lys Val Ala Val Trp Gly Pro Phe
    210                 215                 220

Val Leu Ile Ser Leu Asp Arg Ser Leu Glu Glu Gly Gly Asp Val Gly
225                 230                 235                 240

Thr Glu Trp Leu Gly Thr Ser Ala Glu Asp Val Lys Ala His Ala Phe
                245                 250                 255

Asp Pro Ser Leu Gln Phe Ile His Arg Ser Glu Phe Pro Met Glu Ser
                260                 265                 270

Asn Trp Lys Ile Phe Ser Asp Asn Tyr Leu Asp Ser Ser Tyr His Val
            275                 280                 285

Pro Tyr Ala His Lys Tyr Tyr Ala Thr Glu Leu Asn Phe Asp Thr Tyr
    290                 295                 300

Asp Thr Gln Met Ile Glu Asn Val Thr Ile Gln Arg Val Glu Gly Ser
305                 310                 315                 320

Ser Asn Lys Pro Asp Gly Phe Asp Arg Val Gly Ile Gln Ala Phe Tyr
                325                 330                 335

Ala Phe Ala Tyr Pro Asn Phe Ala Val Glu Arg Tyr Gly Pro Trp Met
                340                 345                 350

Thr Thr Met His Ile His Pro Leu Gly Pro Arg Lys Cys Lys Leu Val
            355                 360                 365

Val Asp Tyr Tyr Ile Glu Asn Ser Met Leu Asp Asp Lys Asp Tyr Ile
    370                 375                 380

Glu Lys Gly Ile Ala Ile Asn Asp Asn Val Gln Arg Glu Asp Val Val
385                 390                 395                 400

Leu Cys Glu Ser Val Gln Arg Gly Leu Glu Thr Pro Ala Tyr Arg Ser
                405                 410                 415

Gly Arg Tyr Val Met Pro Ile Glu Lys Gly Ile His His Phe His Cys
                420                 425                 430

Trp Leu Gln Gln Thr Leu Lys
            435

<210> SEQ ID NO 3
<211> LENGTH: 1751
<212> TYPE: DNA
<213> ORGANISM: Beta vulgaris

<400> SEQUENCE: 3
ctcgtgccga attcggcacg agaaaatcta gtaacaatgg cagcaagtgc tacaaccatg      60
ttgctcaaat acccaactct ttgtgctatg ccaaattcct cttcatcttc aaacaacaac     120
gatcttccta ctagcattcc tcttaataac aataacaatt tattatcaaa caaaaacaaa     180
attcttcaaa caccaaatat taatacttct actaataaaa tcatcactaa agctgttgct     240

-continued

```
tcccctgttt ttccaactct aaaaaccaca tccaacacac cttcttccat tcgatcactt    300
gttcatgaat tcgaccccga aattccacct gaagatgctc ttacacctcc tagtacttgg    360
tacactgagc ctgccttta ttcccatgaa cttgaacgta tcttttacaa aggatggcaa    420
gttgcaggct actctgagca agtaaaggag aaaaatcaat atttcactgg cagtttaggg    480
aatgttgaat atttagtatc tcgagatggt caaggcgaac ttcatgcatt tcacaatgtt    540
tgtacacatc gtgcatcaat tcttgcttgt ggaagtggca aaaagtcatg tttcgtatgc    600
ccttaccatg gatgggtgta tggcttagat ggatcactcg ccaaagccag caaagcaact    660
gaaacacaaa atttggatcc taaagaactt gggcttgcac ccctaaaagt tgcagaatgg    720
ggcccattca ttcttatcag cttggaccga tctctagatg ctaatgctga tgttggaaca    780
gagtggattg gtaaatctgc agaagatgtt aaggcccatg cttttgatcc taatctaaag    840
ttcacccata gaagtgaatt cccaatggaa tgcaactgga aggttttctg tgataactat    900
ctggatagct cttaccatgt tccttatgct cacaaatact atgcagctga actcgacttt    960
gacacttaca acactgaaat gatcgagaaa tgtgtgattc aaagagttgg tagcagttca   1020
aacaagccag atggatttga tagacttgga actgaagcat tctatgcttt tatttacccc   1080
aactttgctg tggaaaggta tggcacttgg atgactacaa tgcatgtcgt tcctatggga   1140
caaaggaaat gcaaactagt ggtggactat tatcttgaga aagccatgtt ggacgacaag   1200
gcttacattg acaagggcat agcaatcaac gataacgtgc agaaggaaga taaggtgttg   1260
tgtgaaagtg tccaaagggg actggagaca ccagcatacc gcagtggcag atatgtgatg   1320
ccaattgaga aaggaatcca ccacttccac tgttggttgc atgaaacttt gcagtgattt   1380
tcgggagctt atttctatgg ttttaccatg tcacattaat aatataattg atgttgggtt   1440
gagcctatgc tcctcatgca attaagttat tttgtggtca tgggaaaacc cttccatttc   1500
tagtatagta gtagtgtctg gtgctaatgt cccatataaa taaagccat agcacctagt   1560
ttccccttca aagttatatc ctaaatattt atggggaaca tatgagattg agtatgaaca   1620
ttttatctag gcatatgtgt gattttaat ttctttgaac aatgagggta agattttgt    1680
ggatgttcgt cagattttat tttactattt atagtagaaa ttgctccaat tataaaaaaa   1740
aaaaaaaaa a                                                          1751
```

<210> SEQ ID NO 4
<211> LENGTH: 446
<212> TYPE: PRT
<213> ORGANISM: Beta vulgaris

<400> SEQUENCE: 4

```
Met Ala Ala Ser Ala Thr Thr Met Leu Leu Lys Tyr Pro Thr Leu Cys
  1               5                  10                  15

Ala Met Pro Asn Ser Ser Ser Ser Asn Asn Asn Asp Leu Pro Thr
             20                  25                  30

Ser Ile Pro Leu Asn Asn Asn Asn Leu Leu Ser Asn Lys Asn Lys
         35                  40                  45

Ile Leu Gln Thr Pro Asn Ile Asn Thr Ser Thr Asn Lys Ile Ile Thr
     50                  55                  60

Lys Ala Val Ala Ser Pro Val Phe Pro Thr Leu Lys Thr Thr Ser Asn
 65                  70                  75                  80

Thr Pro Ser Ser Ile Arg Ser Leu Val His Glu Phe Asp Pro Glu Ile
                 85                  90                  95

Pro Pro Glu Asp Ala Leu Thr Pro Pro Ser Thr Trp Tyr Thr Glu Pro
```

```
                100             105             110
Ala Phe Tyr Ser His Glu Leu Glu Arg Ile Phe Tyr Lys Gly Trp Gln
            115                 120             125

Val Ala Gly Tyr Ser Glu Gln Val Lys Glu Lys Asn Gln Tyr Phe Thr
130             135                     140

Gly Ser Leu Gly Asn Val Glu Tyr Leu Val Ser Arg Asp Gly Gln Gly
145                 150             155                 160

Glu Leu His Ala Phe His Asn Val Cys Thr His Arg Ala Ser Ile Leu
                165                 170             175

Ala Cys Gly Ser Gly Lys Lys Ser Cys Phe Val Cys Pro Tyr His Gly
            180             185                 190

Trp Val Tyr Gly Leu Asp Gly Ser Leu Ala Lys Ala Ser Lys Ala Thr
        195             200             205

Glu Thr Gln Asn Leu Asp Pro Lys Glu Leu Gly Leu Ala Pro Leu Lys
        210             215             220

Val Ala Glu Trp Gly Pro Phe Ile Leu Ile Ser Leu Asp Arg Ser Leu
225             230             235             240

Asp Ala Asn Ala Asp Val Gly Thr Glu Trp Ile Gly Lys Ser Ala Glu
            245             250             255

Asp Val Lys Ala His Ala Phe Asp Pro Asn Leu Lys Phe Thr His Arg
            260             265             270

Ser Glu Phe Pro Met Glu Cys Asn Trp Lys Val Phe Cys Asp Asn Tyr
        275             280             285

Leu Asp Ser Ser Tyr His Val Pro Tyr Ala His Lys Tyr Tyr Ala Ala
        290             295             300

Glu Leu Asp Phe Asp Thr Tyr Asn Thr Glu Met Ile Glu Lys Cys Val
305             310             315             320

Ile Gln Arg Val Gly Ser Ser Asn Lys Pro Asp Gly Phe Asp Arg
            325             330             335

Leu Gly Thr Glu Ala Phe Tyr Ala Phe Ile Tyr Pro Asn Phe Ala Val
            340             345             350

Glu Arg Tyr Gly Thr Trp Met Thr Thr Met His Val Val Pro Met Gly
            355             360             365

Gln Arg Lys Cys Lys Leu Val Val Asp Tyr Tyr Leu Glu Lys Ala Met
        370             375             380

Leu Asp Asp Lys Ala Tyr Ile Asp Lys Gly Ile Ala Ile Asn Asp Asn
385             390             395             400

Val Gln Lys Glu Asp Lys Val Leu Cys Glu Ser Val Gln Arg Gly Leu
            405             410             415

Glu Thr Pro Ala Tyr Arg Ser Gly Arg Tyr Val Met Pro Ile Glu Lys
            420             425             430

Gly Ile His His Phe His Cys Trp Leu His Glu Thr Leu Gln
        435             440             445

<210> SEQ ID NO 5
<211> LENGTH: 25
<212> TYPE: DNA
<213> ORGANISM: synthetic
<220> FEATURE:
<221> NAME/KEY: modified_base
<222> LOCATION: (3)
<223> OTHER INFORMATION: inosine
<221> NAME/KEY: variation
<222> LOCATION: (15)
<223> OTHER INFORMATION: a, g, c, or t/u
<221> NAME/KEY: modified_base
<222> LOCATION: (21)
```

```
<223> OTHER INFORMATION: inosine

<400> SEQUENCE: 5
ccngarcara ayytngaycc naarg                                          25

<210> SEQ ID NO 6
<211> LENGTH: 28
<212> TYPE: DNA
<213> ORGANISM: synthetic

<400> SEQUENCE: 6
ccatcatrtt ytcytchatr tartartc                                       28
```